United States Patent [19]

Pirotzky et al.

[11] Patent Number: 4,927,825
[45] Date of Patent: May 22, 1990

[54] 2-METHOXYCARBONYL SUBSTITUTED N,N'-DI-(TRIMETHOXYBENZOYL) PIPERAZINES, PROCESS FOR PREPARING THE SAME AND THERAPEUTICAL COMPOUNDS CONTAINING THEM

[75] Inventors: Eduardo Pirotzky, Paris, France; Georges Dive, Tilff, Belgium; Jean-Jacques Godfroid; Francoise Heymans, both of Paris, France

[73] Assignee: Societe de Conseils de Recherches et d'Applications Scientifiques (S.C.R.A.S.), France

[21] Appl. No.: 418,113

[22] Filed: Oct. 6, 1989

[30] Foreign Application Priority Data

Oct. 11, 1988 [GB] United Kingdom ............... 8823776

[51] Int. Cl.$^5$ ............... A61K 31/495; C07D 295/08; C07D 295/10
[52] U.S. Cl. ............... 514/255; 544/386; 544/387
[58] Field of Search ............... 544/387, 386; 514/255

[56] References Cited

U.S. PATENT DOCUMENTS 3,318,876  5/1967  Cignarella et al. ............... 544/386
4,420,482  12/1983  Milani et al. ............... 544/387
4,824,996  4/1989  McGregor et al. ............... 544/386

FOREIGN PATENT DOCUMENTS 284359  9/1988  European Pat. Off. ............ 544/387

*Primary Examiner*—Cecelia Shen
*Attorney, Agent, or Firm*—Lucas & Just

[57] ABSTRACT

This invention relates to piperazine derivatives having the general formula I:

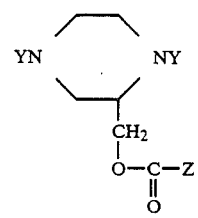

wherein Y stands for

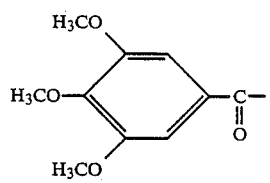

and Z represents various substituents, to a preparation process of said compounds and to therapeutic compositions containing them as an active ingredient.

2 Claims, No Drawings

2-METHOXYCARBONYL SUBSTITUTED N,N'-DI-(TRIMETHOXYBENZOYL) PIPERAZINES, PROCESS FOR PREPARING THE SAME AND THERAPEUTICAL COMPOUNDS CONTAINING THEM

This invention relates to piperazine derivatives having the general formula I:

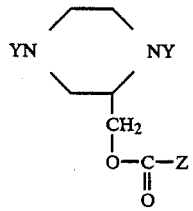

wherein Y stands for

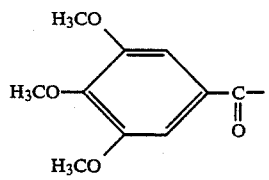

and Z represents either a substituent A wherein A represents a straight or branched alkyl chain having from 1 to 17 carbon atoms; a cycloalkyl group having from 5 to 10 carbon atoms or a group of the general formula:

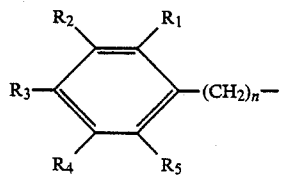

wherein n is zero or an integer of from 1 to 5 and either each of $R_1$, $R_2$, $R_3$, $R_4$, and $R_5$, independently, represents a hydrogen, a chlorine or a bromine atom, a trifluoromethyl, a trifluoromethylthio or a trifluoromethoxy, a methyl or a methoxy group or a substituent NH-A wherein A is as above defined.

The invention also relates to a preparation process of the compounds of formula I, said process comprising reacting a compound of formula

when Z=A or A-N=C=O
when Z=NH-A, wherein A is as above defined, with N,N'-dibenzyl 2-hydroxymethyl piperazine. The reaction is suitably carried out, in the presence of triethylamine, in an aprotic solvent, such as diethyl ether, tetrahydrofuran, benzene or toluene, at room temperature, when Z stands for

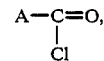

or in benzene or toluene, at 80° C., when Z stands for A-N=C=O.

The corresponding trisubstituted piperazine obtained, of formula II:

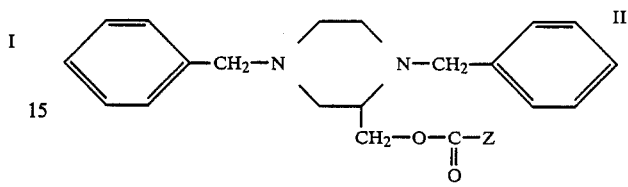

is then hydrogenolized in the presence of Pd/charcoal (in ethanol) leading to the monosubstituted piperazine of formula III:

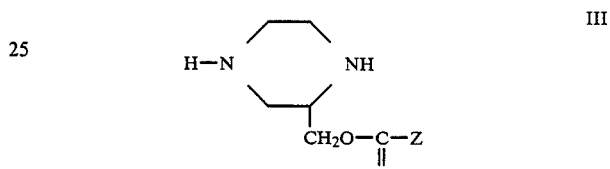

which is di N substituted by treatment with 3,4,5-trimethoxybenzoyl chloride, in benzene, in the presence of triethylamine, at room temperature, to give I.

The invention finally relates to therapeutic compositions of matter containing one of the compounds I, as an active ingredient therein. These compounds are active as anti-ischemic and anti-inflammatory, in various fields, for instance in renal diseases.

EXAMPLE 1

N, N'-di-(3',4',5'-trimethoxybenzoyl)-2-cyclohexylcarbonyloxymethyl piperazine

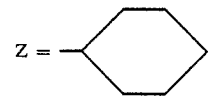

Step A

Preparation of N,N'-dibenzyl 2-cyclohexylcarbonyloxymethyl piperazine

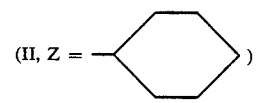

A solution of 2 g (6,8 mmoles) of N,N'-dibenzyl 2-hydroxymethyl piperazine in 30 ml dry benzene and 1 ml of triethylamine was added dropwise to 1,1 g (6,8 mmoles) of cyclohexane carbonyl chloride in 10 ml benzene. After stirring overnight, at room temperature, the solvents were eliminated under reduced pressure and the crude residue treated by $CHCl_3$ was washed with $H_2O$, dilute $NaHCO_3$ then $H_2O$. The organic layer was then dried ($MgSO_4$) evaporated and chromatographed on a silica gel column using diethyl ether/petroleum ether (10:90, in vol.) as eluent. This purification leaded to 1.87 g (68 %) of the title compound as an oil.

IR (film): 3090, 3070, 3030 (ArC-H), 2940, 2860, 2810 (C-H), 1735 (C=O), 1600 (ArC=C) cm$^{-1}$.

$^1$HNMR (80 MHz, CDCl$_3$, HMDS) δ ppm: 7.27 (large s, 10H, ArH), 4.55 (m, 2H, CH$_2$OC=O), 4.12-3.25 (m, 5H, CH$_2$Φ+CH-N), 2.95-2.02 (m, 7H, CH$_2$ piperazine+CH-C=O), 1.72 (m, 4H, CH$_2$-C-C=O), 1.25 (m, 6H, CH$_2$ cyclohexyl).

Step B

Preparation of 2-cyclohexylcarbonyloxymethyl piperazine

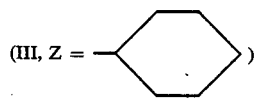

A solution of 1.5 g (3.7 mmoles) of the compound prepared in step A and 50 mg Pd(10 %)/charcoal in 50 ml ethanol was treated with H$_2$ under pressure of 2.8 bars with stirring at 40° C. overnight. After filtration, the ethanol was evaporated under reduced pressure and the crude residue purified on a silica gel column using MeOH/CHCl$_3$ (5:95, in vol.) as eluent. This operation yielded 0.75 g (90 %) of the title compound as a very hygroscopic product.

IR (film): 3340 (N-H), 2960, 2860 (C-H), 1730 (C=O) cm$^{-1}$. $^1$HNMR (80 MHz, CDCl$_3$, HMDS) δ ppm: 3.95 (d, 2H, CH$_2$OC=O), 3.72-3.27 (m, $^1$H, CH-N), 3.45 (s, 2H, disappear with D$_2$O, NH), 3.25-2.27 (m, 7H, CHC=O+CH$_2$ piperazine), 1.62 (m, 4H, CH$_2$-C-C=O), 1.2 (m, 6H, CH$_2$ cyclohexyl).

Step C

Preparation of N,N'-di-(3',4',5'-trimethoxybenzoyl)-2-cyclohexylcarbonyloxymethyl piperazine

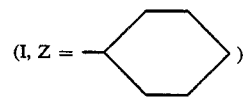

A solution of 0.5 g (2.2 mmoles) of the compound prepared in step B in 30 ml of dry benzene and 1.5 ml triethylamine was added dropwise to 1 g (4.6 mmoles) of 3,4,5-trimethoxybenzoyl chloride in 10 ml of dry benzene. The mixture was kept overnight under stirring at room temperature. The excess of acyl chloride was then decomposed by the addition of 1 ml of EtOH. After evaporation of the solvents under reduced pressure, the residue was treated by CHCl$_3$, washed with H$_2$O, diluted NaHCO$_3$ then H$_2$O. After drying (MgSO$_4$) and evaporation of the chloroform, a purification on a silica gel column using MeOH/CHCl$_3$ (0.5:99.5, in vol.) yielded 1.1 g (74 %) of the title compound as a wax.

IR (film): 3050, 3000 (ArCH), 2940, 2860 (C-H), 1720 (C=O ester), 1650 (C=O amide), 1585 (ArC=C) cm$^{-1}$. $^1$HNMR (60 MHz, CDCl$_3$, HMDS) δ ppm: 6.57 (s, 4H, ArH), 4.83 (d, 2H, CH$_2$0C=O), 4.45-3.97 (m, 3H, O=C NCH$_2$-CH-NC=O), 3.86 (large s, 18H, CH$_3$O), 3.5-2.66 (m, 4H, CH$_2$NC=O), 2.6-2.23 (m, $^1$H, CHC=O), 1.93-0.9 (m, 10H, CH$_2$ cyclohexyl).

EXAMPLE 2

N,N'-di-(3',4',5'-trimethoxybenzoyl)-2-tert-butyl carbonyloxymethyl piperazine Z=C(CH$_3$)$_3$ The title compound was obtained as described in example 1 steps A, B, C but starting with 2,2-dimethylpropanoylchloride instead of cyclohexancarbonylchloride as waxy compound.

IR (film): 3060 (ArC-H), 2960, 2840 (C-H),1730 (C=O ester), 1640 (C=O amide), 1585 (ArC=C) cm$^{-1}$.

$^1$HNMR (60 MHz, CDCl$_3$, HMDS) δ ppm: 6.63 (s, 4H, ArH), 4.93-4.5 (m, 2H, CH$_2$OC=O), 4.43-3.96 (m, 3H, O=CNCH$_2$ CHNC=O), 3.86 (s, 18 H, CH$_3$O), 3.5-2.8 (m, 4H, CH$_2$NC=O), 1.06 (s, 9H, CH$_3$).

EXAMPLE 3

N,N'-di-(3',4',5',-trimethoxybenzoyl)-2-n-butanoyloxymethyl piperazine Z=(CH$_2$)$_2$CH$_3$ The title compound was obtained as described in example 1, steps A, B, C but starting with n-butanoylchloride, as an oil.

IR (film): 3080 (ArC-H), 2930-2860 (C-H), 1720 (C=O ester), 1640 (C=O amide), 1585 (ArC=C) cm$^{-1}$.

$^1$HNMR (80 MHz, CDCl$_3$, HMDS) δ ppm: 6.62 (s, 4H, ArH), 4.66 (m, 2H, CH$_2$OC=O), 4.55-4.05 (m, 3H, O=CNCH$_2$CHNC=O), 3.85 (large s, 18H, CH$_3$O), 3.52-2.8 (m, 4H, CH$_2$NCO), 2.3 (m 2H, CH$_2$CO), 1.77-1.35 (m, 2H, CH$_2$-C-C=O), 0.87 (t, 3H, CH$_3$).

EXAMPLE 4

N,N'-di-(3',4',5'-trimethoxybenzoyl)-2-n-octanoyloxymethyl piperazine Z=(CH$_2$)$_6$CH$_3$ The title compound was obtained as described in example 1, steps A, B, C but starting with n-octanoylchloride. Viscous compound.

IR (film): 3060, 3000 (ArC=H), 2940, 2860 (C-H), 1735 (C=O ester), 1640 (C=O amide), 1585 (ArC=C) cm$^{-1}$.

$^1$HNMR (80 MHz, CDCl$_3$, HMDS) δ ppm: 6.62 (s, 4H, ArH), 4.85-4.05 (m, 5H, CH$_2$OC=O+O=CNCH$_2$-CHNCO), 3.77 (s, 18H, CH$_3$O), 3.57-2.7 (m, 4H, CH$_2$NC=O ), 2.2 (t, 2H, CH$_2$C=O), 1.52 (m, 2H, CH$_2$-C-C=O), 1.33 (large s, 8H, (CH$_2$)$_4$), 0.82 (t, 3H, CH$_3$).

EXAMPLE 5

N,N'-di-(3',4',5'-trimethoxybenzoyl)-2-n-decanoyloxymethyl piperazine Z=(CH$_2$)$_8$CH$_3$ The title compound was obtained as described in example 1, steps A, B, C but starting with n-decanoylchloride. Viscous compound.

IR (film): 3060 (ArC-H), 2920, 2850 (C-H), 1740 (C=O ester), 1635 (C=O amide), 1580 (ArC=C) cm$^{-1}$.

$^1$HNMR (80 MHz, CDCl$_3$, HMDS) δ ppm: 6.6 (s, 4H, ArH), 4.6 (m, 2H, CH$_2$0C=O), 4.45-3.97 (m, 3H, O=CNCH$_2$-CH-NC=O), 3.87 (s, 18H, CH$_3$O), 3.65-2.85 (m, 4H, CH$_2$NC=O), 2.12 (t, 2H, CH$_2$C=O), 1.42 (m, 2H, CH$_2$-C-C=O), 0.75 (t, 3H, CH$_3$).

EXAMPLE 6

N,N'-di-(3',4',5'-trimethoxybenzoyl)-2-octadecanoyloxymethyl piperazine Z=(CH$_2$)$_{16}$CH$_3$ The title compound was obtained as described in example 1, steps A, B, C but starting with octadecanoyl chloride. Viscous oil.

IR (film): 3020 (ArC=H), 2940, 2870 (C H), 1725 (C=O ester), 1650 (C=O amide), 1595 (ArC=C) cm$^{-1}$.

$^1$H NMR (80 MHz, CDCl$_3$, HMDS) δ ppm: 6.57 (s, 4H, ArH), 4.75-4.0 (m, 5H, CH$_2$OC=O+O=CNCH$_2$CHNC=O), 3.87 (s, 9H, CH$_3$O), 3.48-2.75 (m, 4H, CH$_2$NC=O), 2.22 (t, 2H, CH$_2$C=O), 1.47 (m, 2H, CH$_2$C-C=O), 1.21 (large s, 28H, (CH$_2$)$_{14}$), 0.77 (t, 3H, CH$_3$).

EXAMPLE 7

N,N'-di-(3',4',5',-trimethoxybenzoyl)-2-ortho-chlorobenzoyloxymethyl piperazine

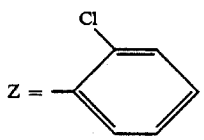

The title compound was obtained as described in example 1, steps A, B, C but starting with 2-chlorobenzoyl chloride. Oily product.

IR (film): 3070, 3020 (ArC-H), 2930, 2860 (C-H), 1720 (C=O ester), 1630 (C=O amide), 1590 (ArC=C) cm$^{-1}$.

$^1$HNMR (60 MHz, CDCl$_3$, HMDS) δ ppm: 7.63-7.13 (m, 4H, chlorophenyl H), 6.56 (d, 4H, trimethoxyphenyl Ar-H), 4.83 (m, 2H, CH$_2$OC=O), 4.63-3.96 (m, 3H, O=CNCH$_2$-CHNC=O), 3.8 (s, 18H, CH$_3$O), 3.5-2.73 (m, 4H, CH$_2$NC=O).

EXAMPLE 8

N,N'-di-(3',4',5'-trimethoxybenzoyl)-2-N"-(n-butyl)-carbamoyloxymethyl piperazine Z: NH-(CH$_2$)$_3$-CH$_3$

Step A

Preparation of N,N'-dibenzyl 2-N"-(n-butyl)carbamoyloxymethyl piperazine (II, Z=NH(CH$_2$)$_4$CH$_3$)

A mixture of 10 g (34 mmoles) of N,N'-dibenzyl 2-hydroxymethyl piperazine, 10 g (102 mmoles) of n-butylisocyanate and 15 ml of triethylamine in 100 ml of dry benzene was refluxed under stirring for 48 hours. After evaporation of the solvents, the crude residue was treated by CHCl$_3$, washed with H$_2$O, dilute NaHCO$_3$ then H$_2$O. The chloroformic layer was dried (MgSO$_4$), concentrated under reduced pressure and purified on a silica gel column using diethyl ether/petroleum ether (10:90, in vol.) as eluent to give 11,7 g (87 %) of the title compound as an oil.

IR (film): 3330 (N-H), 3080, 3060, 3020 (ArC-H), 2940, 2860 (C-H), 1720 (C=O urethane). $^1$HNMR (80 MHz, CDCl$_3$, HMDS) δ ppm: 7.27 (large s, 10H, ArH), 4.63 (m, 1H, NH), 4.37 (m, 2H, CH$_2$OC=O), 4.02 and 3.63 (2 s, 4H, CH$_2$O), 3.28-2.45 (m, 9H, piperazine+CH$_2$NC=O), 1.52-1.02 (m, 4H, (CH$_2$)$_2$), 0.82 (t, 3H, CH$_3$).

Steps B and C

The title compound was obtained as described in example 1, steps B and C. It appeared as white crystals, mp 90° C.

IR (nujol): 3340 (N-H), 1720 (C=O methane), 1635 (C=O amide), 1590 (ArC=C) cm$^{-1}$.

$^1$HNMR (80 MHz, CDCl$_3$, HMDS) δ ppm: 6.6 (s, 4H, ArH), 4.72 (m, 2H, CH$_2$OC=O), 4.65-3.92 (m, 4H, O=CNCH$_2$CHNC=O+NH), 3.87 (large s, 18H, CH$_3$O), 3.42-2.7 (m, 6H, CH$_2$NC=O), 1.3 (m, 4H, (CH$_2$)$_2$), 0.8 (t, 3H, CH$_3$).

EXAMPLE 9

N,N'-di-(3',4',5'-trimethoxybenzoyl)-2-N"-(3',4',5'-trimethoxyphenyl)-carbamoyloxymethyl piperazine

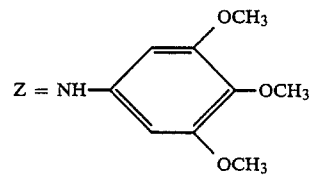

The title compound was obtained as described in example 8 for step A, but starting with equimolar quantities of N,N'-dibenzyl 2-hydroxymethyl piperazine and 3,4,5-trimethoxyphenyl isocyanate instead of n-butyl isocyanate. Steps B and C were as in example 1, steps B and C. The title compound was a pale yellow solid, mp =122° C.

IR (nujol): 3300 (N-H), 1735 (C=O urethane), 1630 (C=O amide), 1590 (ArC=C) cm$^{-1}$.

$^1$HNMR (80 MHz, CDCl$_3$, HMDS) δ ppm: 6.80 (m, 1H, NH), 6.62 (m, 6H, ArH), 4.9-4.52 (m, 2H, CH$_2$OC=O), 4.47-3.97 (m, 3H, O=CNCH$_2$-CHNC=O), 3.58-2.75 (m, 4H, CH$_2$NC=O).

According to the same process as described in example 1, steps A,B,C, the following compounds were prepared (only modifications of the $^1$HNMR spectra are given):

EXAMPLE 10

N,N'-di-(3',4',5'-trimethoxybenzoyl)-2-(2'-ethyl)-butanoyloxymethyl piperazine

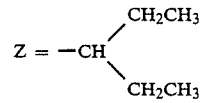

mp=170.2° C.

$^1$HNMR δ ppm: 2.12 (quintet, 1H, CHEt$_2$), 1.47 (quintet, 4H, CH$_2$CH$_3$), 0.77 (t, 6H, CH$_3$).

EXAMPLE 11

N,N'-di-(3',4',5'-trimethoxybenzoyl)-2-n-hexanoyloxymethyl piperazine Z=-(CH$_2$)$_4$CH$_3$ waxy solid.

$^1$HNMR δ ppm: 2.27 (m, 2H, CH$_2$C=O), 1.51 (m, 2H, CH$_3$-C-C=O), 1.25 (m, 4H, CH$_2$), 0.77 (t, 3H, CH$_3$).

EXAMPLE 12

N,N'-di-(3',4',5'-trimethoxybenzoyl)-2-acetyloxymethyl piperazine Z=-CH$_3$
mp=59° C.

$^1$HNMR δ ppm: 1.93 (s, 3H, CH$_3$C=O).

EXAMPLE 13

N,N'-di-(3',4',5'-trimethoxybenzoyl)-2-tert-butyl acetyloxymethyl piperazine Z=-CH$_2$C(CH$_3$)$_3$ mp: 86.6° C.
¹HNMR δ ppm: 2.05 (s, 2H, CH₂C=O), 0.92 (s, 9H, CH₃).

According to the same process as described in example 8, steps A,B,C, the following compounds were prepared (only modifications of the ¹HNMR spectra are given):

EXAMPLE 14

N,N'-di-(3',4',5'-trimethoxybenzoyl)-2-N''-(1'-ethyl)-propyl carbamoyloxymethyl piperazine

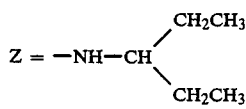

mp=90.2° C.
¹HNMR δ ppm: 3.55–2.92 (m, 5H, CH₂NC=O+CHN COO), 1.37 (m, 4H, CH₂CH₃), 0.82 (t, 6H, CH₃).

EXAMPLE 15

N,N'-di-(3',4',5'-trimethoxybenzoyl)-2-N''-tert-butyl carbamoyloxymethyl piperazine Z=NH-C(CH₃)₃ viscous compound.
¹HNMR δ ppm: 1.20 (s, 9H, CH₃).

EXAMPLE 16

N,N'-di-(3',4',5'-trimethoxybenzoyl)-2-N''-tert-amyl carbamoyloxymethyl piperazine Z=-NH-CH₂-C(CH₃)₃
mp=80° C.
¹HNMR δ ppm: 0.80 (s, 9H, CH₃).

EXAMPLE 17

N,N'-di-(3',4',5'-trimethoxybenzoyl)-2-N''-ortho-chlorophenyl carbamoyloxymethyl piperazine

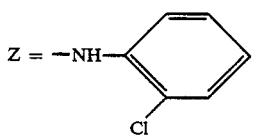

mp=115° C.
¹HNMR δ ppm: 7.3 and 6.7 (2 s, 4H, C₆H₄), 6.67–6.42 (m, 4H, C₆H₂).

EXAMPLE 18

N,N'-di-(3',4',5'-trimethoxybenzoyl)-2-N''-(1'-methyl)-butyl carbamoyloxymethyl piperazine

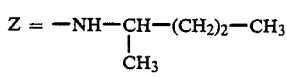

mp =78° C.
¹HNMR ppm: 1.27 (m, 4H, CH₂), 1.02 (d, 3H, CH₃CH), 0.85 (t, 3H, CH₃).

EXAMPLE 19

N,N'-di-(3',4',5'-trimethoxybenzoyl)-2-N''-(1',2',2'-trimethyl)-propyl carbamoyloxymethyl piperazine

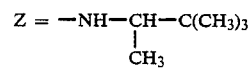

mp=86° C.
¹HNMR δ ppm: 0.92 (m, 3H, CH₃CH), 0.79 (s, 9H, CH₃C).

EXAMPLE 20

N,N'-di-(3',4',5'-trimathoxybenzoyl)-2-N''-(3'-methyl)-butyl carbamoyloxymethyl piperazine

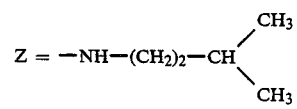

mp=71° C.
¹HNMR δ ppm: 2.17–1.80 (m, 1H, CH(CH₃)₂), 1.27 (m, 2H, CH₂), 0.80 (d, 6H, CH₃).

EXAMPLE 21

N,N'-di-(3',4',5'-trimethoxybenzoyl)-2-N''-(1',3'-dimethyl)butyl carbamoyloxymethyl piperazine

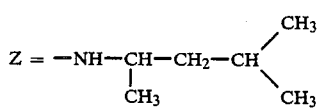

mp=76° C.
¹HNMR δ ppm: 2.35–1.91 (m, 1H, CH(CH₃)₂), 1.18 (m, 2H, CH₂), 098 (d, 3H, CH₃ -C-N), 0.78 (d, 6H, CH₃).

EXAMPLE 22

N,N'-di-(3',4',5'-trimethoxybenzoyl)-2-N''-(2'-methyl)-butyl carbamoyloxymethyl piperazine

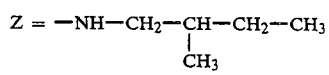

mp=70° C.
¹HNMR δ ppm: 1.70 (m, 1H, CH), 1.22 (m, 2H, CH₂), 0.85 (m, 6H, CH₃).

TOXICOLOGY

The compounds of the invention have been administrated per os to mice for determination of acute LD₅₀. For all the compounds of the invention, LD₅₀ was over 700 mg/kg.

PHARMACOLOGY

A proof of the pharmaceutical interest of the compounds of the invention has been established by the following pharmaceutical experimentation:

Inhibition of the platelets aggregation on New Zealand rabbits.

The experimentation was conducted on platelets with plasma of New Zealand rabbits. Blood samples were taken from auricular artery and placed in a citrate buffer (3.8% pH 7.4); blood was further centrifugated for 15 mn at 1 200 RPM.

The tested sample was prepared in DMSO, then poured on platelets rich plasma for 1 mn, then a dose of 2.5 nM of PAF was added.

The determination is made on a Cronolog Coultronics apparatus which determines the transmission percentage corresponding to the maximum height of the peak before the desaggregation.

The percentage of variation of the inhibition with respect to the transmission percentage is calculated (control: pure DMSO).

This method was described in details in LABORATORY INVESTIGATIONS, Vol. 41, No. 3, p. 275, 1979, JEAN-PIERRE CAZENAVE, Dr. MED., JACQUES BENVENISTE, DR. MED., AND J. FRASER MUSTARD, M.D., "Aggregation of rabbits platelets by platelet-activating factor is independent of the release reaction and the arachidonate pathway and inhibited by membrane-active drugs".

The results demonstrate that the compounds inhibit the aggregation induced by 2.5 nM of PAF. Twenty-two tests made on 22 different rabbits allowed us to calculate the $IC_{50}$ of the various compounds using the linear regression test.

The values for $IC_{50}$ on platelets have been found as follows:

| Example 1:  | 2.80 | $.10^{-7}$ |
| Example 2:  | 1.00 | $.10^{-7}$ |
| Example 3:  | 3.60 | $.10^{-6}$ |
| Example 4:  | 3.14 | $.10^{-7}$ |
| Example 5:  | 2.82 | $.10^{-6}$ |
| Example 6:  | 4.5  | $.10^{-5}$ |
| Example 7:  | 1.69 | $.10^{-7}$ |
| Example 8:  | 2.41 | $.10^{-7}$ |
| Example 9:  | 1.38 | $.10^{-5}$ |
| Example 10: | 7.12 | $.10^{-8}$ |
| Example 11: | 4.97 | $.10^{-6}$ |
| Example 12: | 4.3  | $.10^{-7}$ |
| Example 13: | 1.21 | $.10^{-7}$ |
| Example 14: | 1.34 | $.10^{-7}$ |
| Example 15: | 1.34 | $.10^{-7}$ |
| Example 16: | 1.05 | $.10^{-6}$ |
| Example 17: | 2.12 | $.10^{-5}$ |
| Example 18: | 1.04 | $.10^{-7}$ |
| Example 19: | 1.69 | $.10^{-7}$ |
| Example 20: | 1.37 | $.10^{-7}$ |
| Example 21: | 2.82 | $.10^{-7}$ |
| Example 22: | 4.73 | $.10^{-7}$ |

PRESENTATION - POSOLOGY

In human therapy, active doses are 1–50 mg/kg per day in oral administration (tablets or gelatine capsules containing 50 mg or 100 mg per unit doses, for instance) or 0.1 to 5 mg/kg in IV administration (unit doses of 5 to 100 mg in individual phials).

We claim:

1. Piperazine derivatives having the formula I:

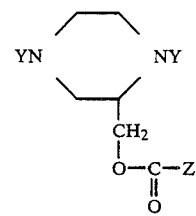

wherein Y stands for

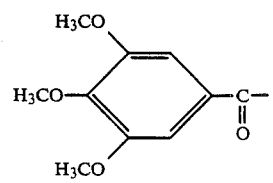

and Z represents either a substituent A wherein A represents a straight or branched alkyl chain having from 1 to 17 carbon atoms; a cycloalkyl group having from 5 to 10 carbon atoms or a group of the formula:

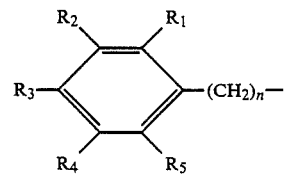

wherein n is zero or an integer of from 1 to 5 and either each of $R_1$, $R_2$, $R_3$, $R_4$, and $R_5$, independently, represents a hydrogen, a chlorine or a bromine atom, a trifluoromethyl, a trifluoromethylthio or a trifluoromethoxy, a methyl or a methoxy group or a substituent NH-A wherein A is as above defined.

2. An anti-ischemic and anti-inflammatory therapeutic composition of matter comprising an effective amount of at least one compound according to claim 1, that is to say, per unit doses, 50 to 100 mg for oral administration or 5 to 100 mg for intravenous administration, associated with the usual excipients for the selected administration route.

* * * * *

UNITED STATES PATENT AND TRADEMARK OFFICE
CERTIFICATE OF CORRECTION

PATENT NO. : 4,927,825

DATED : May 22, 1990

INVENTOR(S) : Edwardo Pirotsky et al.

It is certified that error appears in the above-identified patent and that said Letters Patent is hereby corrected as shown below:

Column 3, line 33, change "$^1$H" to --1H--;
line 62, change "(ArCH)" to --(ArC-H)--;
line 65, change "(d, 2H, $CH_2OC=O$)" to --(d, 2H,$CH_2OC=O$)--;
line 67, change "$^1$H" to --1H--

Column 4, line 39, change "(ArC=H)" to --(ArC-H)--;
line 60, change "($CH_2OC=O$)" to --($CH_2OC=O$)--

Column 5, line 4, change "(ArC=H)" to --(ArC-H)--;
line 4, change "(C H)" to --(C-H)--; line 60, change "(m, $^1$H, NH)" to --(m, 1H, NH,)--

Column 6, line 31, change "$^1$H" to --1H--; line 49, change "(quintet, $^1$H, $CHEt_2$)" to --(quintet, 1H, $CHEt_2$)--;
line 57, change "$CH_3$-C-C=O" to --$CH_2$-C-C=O--

Column 7, line 26, change "Z=NH-C($CH_3$)$_3$" to --Z=-NH-C($CH_3$)$_3$--

Column 8, line 11, change "-trimathoxybenzoyl" to ---trimethoxybenzoyl--;

UNITED STATES PATENT AND TRADEMARK OFFICE
CERTIFICATE OF CORRECTION

PATENT NO. : 4,927,825

DATED : May 22, 1990

INVENTOR(S) : Edwardo Pirotsky et al.

It is certified that error appears in the above-identified patent and that said Letters Patent is hereby corrected as shown below:

Column 8, line 67, change "(3.8% pH 7.4)" to --(3.8%;ph 7.4)--.

Signed and Sealed this

Twentieth Day of August, 1991

*Attest:*

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO. : 4,927,825
DATED : May 22, 1990
INVENTOR(S) : Eduardo Pirotzky et al.

It is certified that error appears in the above-identified patent and that said Letters Patent is hereby corrected as shown below:

On the title page, item [75], at the end of the list of inventors, add the following:

--Pierre Braquet, Garches, France--

Signed and Sealed this

Twenty-second Day of December, 1992

Attest:

DOUGLAS B. COMER

Attesting Officer     Acting Commissioner of Patents and Trademarks